US012343531B2

(12) United States Patent
Müller-Bruhn

(10) Patent No.: US 12,343,531 B2
(45) Date of Patent: Jul. 1, 2025

(54) ELECTRO-MAGNETIC INDUCTION DEVICE AND METHOD OF ACTIVATING A TARGET TISSUE

(71) Applicant: STIMIT AG, Biel/Bienne (CH)

(72) Inventor: Ronja Müller-Bruhn, Windisch (CH)

(73) Assignee: STIMIT AG, Biel/Bienne (CH)

( * ) Notice: Subject to any disclaimer, the term of this patent is extended or adjusted under 35 U.S.C. 154(b) by 460 days.

(21) Appl. No.: 16/968,025

(22) PCT Filed: Feb. 6, 2019

(86) PCT No.: PCT/EP2019/052876
§ 371 (c)(1),
(2) Date: Aug. 6, 2020

(87) PCT Pub. No.: WO2019/154837
PCT Pub. Date: Aug. 15, 2019

(65) Prior Publication Data
US 2021/0361939 A1    Nov. 25, 2021

(30) Foreign Application Priority Data

Feb. 6, 2018  (CH) .................................. 00135/18
Jun. 7, 2018  (CH) .................................. 00733/18

(51) Int. Cl.
*A61N 1/36*        (2006.01)
*A61M 16/00*       (2006.01)
(Continued)

(52) U.S. Cl.
CPC ....... *A61N 1/3601* (2013.01); *A61M 16/0051* (2013.01); *A61M 16/024* (2017.08);
(Continued)

(58) Field of Classification Search
CPC ................ A61N 1/3601; A61N 1/0456; A61N 1/36017; A61N 1/40; A61N 2/002;
(Continued)

(56) References Cited

U.S. PATENT DOCUMENTS 5,857,957 A      1/1999  Lin
6,224,562 B1 *   5/2001  Lurie ................... A61N 1/3601
                                                         607/42

(Continued)

OTHER PUBLICATIONS

International Search Report and Written Opinion of International Application No. PCT/EP2019/052876 issued Apr. 24, 2019.

*Primary Examiner* — Mark W. Bockelman
(74) *Attorney, Agent, or Firm* — MEDLER FERRO WOODHOUSE & MILLS PLLC

(57) ABSTRACT

An electro-magnetic induction device for activating a target tissue in a body via its muscular or neural system includes an electro-magnetic field generator with a coil design configured to generate an electro-magnetic field, a mounting arrangement holding the coil design at the body, a sensor member configured to detect an activation of a target tissue, an electro-magnetic field adjustment mechanism configured to automatically adjust the position and a field strength of the electro-magnetic field, and a calibration unit in communication with the sensor member and the electro-magnetic field adjustment mechanism. The calibration unit is configured to control the electro-magnetic field adjustment mechanism to automatically vary the position and the field strength of the electro-magnetic field, to receive an activation feedback signal from the sensor, and to control the electro-magnetic field adjustment mechanism to automatically stop variation of the position of the electro-magnetic field generated by the coil design.

25 Claims, 7 Drawing Sheets

(51) Int. Cl.
*A61M 16/20* (2006.01)
*A61N 1/04* (2006.01)
*A61N 1/40* (2006.01)
*A61N 2/00* (2006.01)
*A61N 2/02* (2006.01)
*A61N 7/00* (2006.01)

(52) U.S. Cl.
CPC ........ *A61M 16/204* (2014.02); *A61M 16/205* (2014.02); *A61N 1/0456* (2013.01); *A61N 1/36017* (2013.01); *A61N 1/40* (2013.01); *A61N 2/002* (2013.01); *A61N 2/006* (2013.01); *A61N 2/02* (2013.01); *A61N 7/00* (2013.01); *A61M 2016/0027* (2013.01); *A61M 2016/0036* (2013.01); *A61M 2205/054* (2013.01); *A61M 2205/057* (2013.01); *A61M 2205/058* (2013.01); *A61M 2210/1014* (2013.01); *A61N 2007/0026* (2013.01)

(58) Field of Classification Search
CPC . A61N 2/006; A61N 2/02; A61N 7/00; A61N 2007/0026; A61N 7/02; A61M 16/0051; A61M 16/024; A61M 16/204; A61M 16/205; A61M 2016/0027; A61M 2016/0036; A61M 2205/054; A61M 2205/057; A61M 2205/058; A61M 2210/1014; A61M 16/0488; A61M 16/0009; A61M 16/0066; A61M 2016/0015; A61H 31/00
See application file for complete search history.

(56) References Cited

U.S. PATENT DOCUMENTS

| | | | |
|---|---|---|---|
| 6,409,694 B1* | 6/2002 | Bugarin | A61F 5/055 |
| | | | 602/18 |
| 2004/0193003 A1 | 9/2004 | Mechlenburg et al. | |
| 2005/0228209 A1* | 10/2005 | Schneider | A61B 5/246 |
| | | | 600/13 |
| 2007/0277826 A1 | 12/2007 | Lurie | |
| 2008/0306325 A1* | 12/2008 | Burnett | A61N 2/02 |
| | | | 600/13 |
| 2011/0230702 A1* | 9/2011 | Honour | A61N 1/36017 |
| | | | 607/42 |
| 2012/0016280 A1 | 1/2012 | Aliverti et al. | |
| 2013/0238050 A1 | 9/2013 | Simon et al. | |
| 2014/0046423 A1* | 2/2014 | Rajguru | A61N 2/02 |
| | | | 607/144 |
| 2015/0231348 A1 | 8/2015 | Lee et al. | |
| 2015/0290476 A1 | 10/2015 | Krocak et al. | |
| 2015/0314133 A1 | 11/2015 | Yamashiro | |
| 2015/0367127 A1 | 12/2015 | Meyyappan et al. | |
| 2016/0310730 A1 | 10/2016 | Martins et al. | |

* cited by examiner

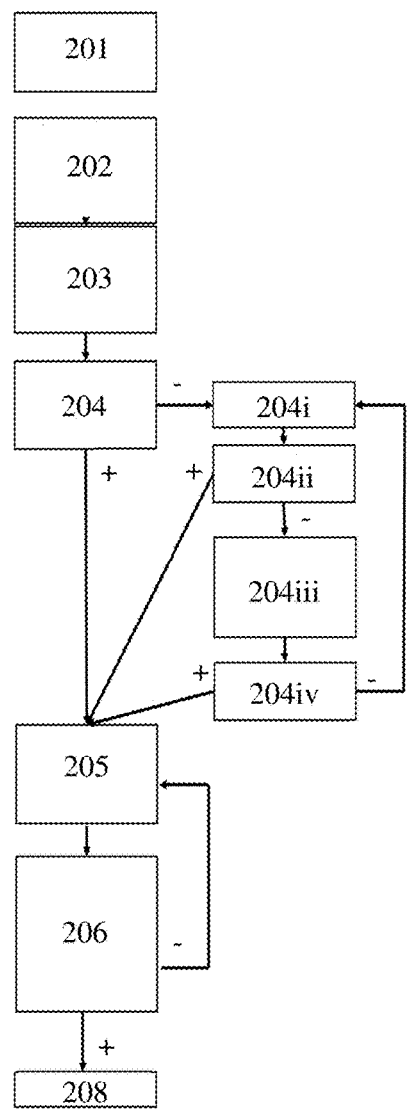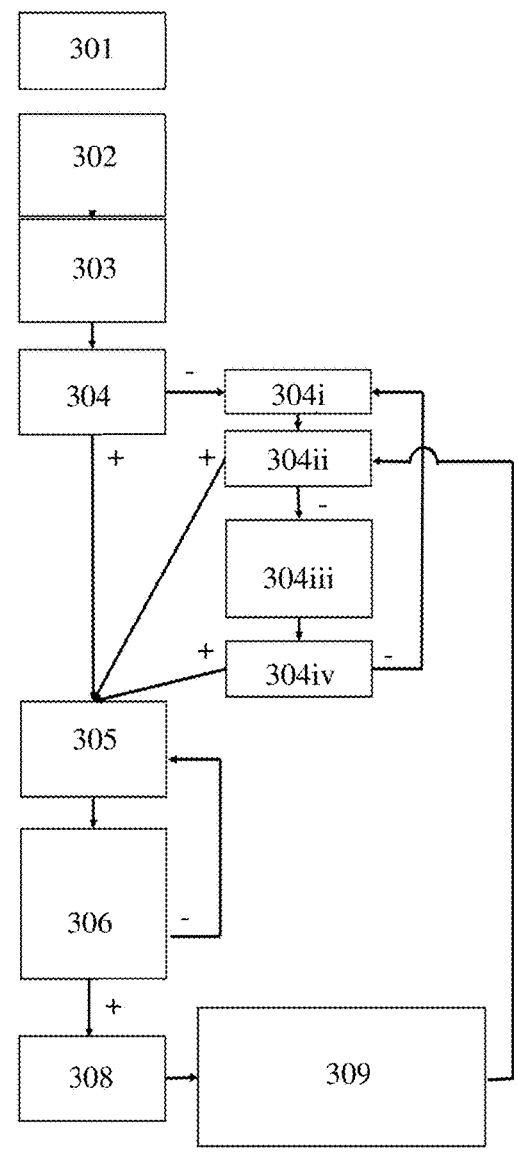
Fig. 11
Fig. 12

ELECTRO-MAGNETIC INDUCTION DEVICE AND METHOD OF ACTIVATING A TARGET TISSUE

TECHNICAL FIELD

The present invention relates to an electro-magnetic induction device according to the preamble of independent claim 1 and more particularly to a process of manufacturing such a device, a method of activating a target tissue and uses of such a device.

BACKGROUND ART

In medicine, it is known that for many purposes it is beneficial to activate a target tissue of a patient. For example, in critical care units of hospitals it may be desired to activate the diaphragm of ventilated patients in order to prevent drawbacks of disuse of the diaphragm. It was shown that disuse atrophy of diaphragm muscle fibers occurs already in the first 18-69 hours of mechanical ventilation, and the muscle fiber cross-sections decreased by more than 50% in this time. Thus, it is aimed to activate the diaphragm repeatedly while the patient is given artificially or mechanical respiration such that the functioning of the diaphragm can be upheld, or to activate the diaphragm at least during the weaning period to support effective restoration of independent respiratory function.

For achieving such activation of tissues in a patient's body, it is known to directly stimulate the tissue or to indirectly activate the tissue via stimulation of specific parts of the neural system. For example, the target tissue being a muscular tissue can be activated by providing electric pulses directly to the tissue or to nerves associated to the tissue. More specifically, it is known that the diaphragm can be activated by stimulating the Phrenic nerve, e.g., at the neck of the patient.

In this context, US 2016/0310730 A1 describes an apparatus for reducing ventilation induced diaphragm disuse in a patient receiving ventilation support from a mechanical ventilator (MV). The apparatus includes an electrode array of first and second types and comprising a plurality of electrodes configured to stimulate a phrenic nerve of the patient, and at least one controller identifying a type of electrode array from at least two different types, and generating a stimulus signal for stimulating a phrenic nerve of the patient based upon the identity of the electrode type. Such electrode-based stimulation is not very robust to patient movements or relocations, and the possible stimulation depth can be significantly limited by bones or fatty tissue. Furthermore, electrode stimulation is reported to be more painful for the patient than electro-magnetic stimulation.

Therefore, there is a need for a system allowing a more convenient and efficient operation as well as less side effects in stimulation.

DISCLOSURE OF THE INVENTION

According to the invention this need is settled by an electro-magnetic induction device as it is defined by the features of a first independent claim, by a process of manufacturing an electro-magnetic induction device as it is defined by the features of a second independent claim, and by a method of transcutaneous electro-magnetic induction of one or more Phrenic nerves as it is defined by the features of a third independent claim. Preferred embodiments are subject of the dependent claims.

In one aspect, the invention is an electro-magnetic induction device for activating a target tissue in a human or animal body via its muscular or neural system, which device comprises (i) an electro-magnetic field generator with coil design configured to generate a spatial electro-magnetic field having a targeted shape, (ii) a mounting arrangement holding the coil design of the electro-magnetic field generator at the human or animal body, (iii) a sensor member configured to detect an activation of the target tissue, (iv) an electro-magnetic field adjustment mechanism configured to automatically adjust the position of the electro-magnetic field generated by the coil design, and (v) a calibration unit in communication with the sensor member and with the electro-magnetic field adjustment mechanism. The coil design described herein can be or comprise at least two coils or at least one cone shaped or otherwise curved or bulged coil, or at least one small coil, i.e. a coil sufficiently small to generate a sharp electro-magnetic field such as a coil having a diameter of 3 cm or less. The targeted shape of the electro-magnetic field described herein can comprise a peak formed by the spatial electro-magnetic field. The electro-magnetic field generator can also be referred to as electro-magnetic field creator. The targeted shape of the electro-magnetic field can be achieved by the electro-magnetic field being a locally constrained, targeted electric field, e.g., having a peak. It can be adapted to be active in a target area being the nerve area or tissue area that shall be activated with the electromagnetic-field (e.g. the phrenic nerve that shall be activated), which can be for example achieved by the peak in the electro-magnetic field (focality area). The targeted shape can generally be any shape of the electro-magnetic field or the time-dependent electric field component that allows to stimulate one or more target nerves effectively while minimizing other undesired co-stimulation effects of surrounding, above-lying or close-by tissues or nerves. A peak shape is such example, because it maximizes effects in a focality area and minimizes effects outside this area.

Thereby, tissue can refer to any type of human tissue, including but not limited to skin or muscle tissue (i.e. diaphragm muscle fibers).

The parameters of the voltage or current waveform applied to the coil by a generator affect the temporal characteristics of the electromagnetic field, including pulse shape, amplitude, width, polarity, and repetition frequency; duration of and interval between bursts or trains of pulses; total number of pulses; and interval between stimulation sessions and total number of sessions have, amongst others, an influence on the field strength and determine if and with which intensity or "dose" a target area or target tissue can be activated. The electro-magnetic field can be generated by the electro-magnetic field generator in single pulses or as a train. Thereby, single pulses relate to the generation of the electro-magnetic field over a comparably short time and with a comparably long interruption between two subsequent pulses. Typically, single pulses are provided at frequencies lower than 10 Hz such as, e.g. at 5 Hz or below, or single pulses are initiated by the user or practitioner. The single pulses can have a time width of about 10 to 300 µs. Such pulses can activate nerves and muscles and are identifiable by the patient or by a sensor. In particular, such single pulses may cause a single convulsion of a muscle. In contrast thereto, when being generated in a train, the electro-magnetic field is either continuously generated or in sequences of pulses comparably quickly following each other. Such pulses can be provided in a frequency range of in between about 15 Hz and about 30 Hz. In particular, a train may achieve to activate a nerve or muscle such that a tetanic contraction or activation is induced. Advantageously, the train is provided by increasing the intensity (field strength) and/or frequency until a target intensity and frequency is achieved (ramp protocol). Like this, sudden convulsion or discomfort can be decreased. All of these parameters are summarized under the term "temporal characteristics" or "temporal parameters" of the electro-magnetic field. These temporal parameters can be adjusted manually via an input interface or be controlled automatically by an adjustment mechanism.

The temporal characteristics and spatial distribution of the electro-magnetic field can be tuned in such a way that the desired activation (activation feedback) of the target area is achieved. Thereby, the activation feedback (signal) refers to a signal that indicates appropriate characteristics of target tissue activation, e.g. a signal that reaches or exceeds a target value (threshold), a signal that exhibits a certain curve pattern or shape, a signal that fulfills a certain algorithm known to represent appropriate target tissue activation in the desired strength, or any combination thereof. The activation feedback (signal) may comprise feedback in particular about a desired muscle activation strength that shall be reached before the adjustment mechanism stops variation. The appropriate activation feedback signal characteristics can for example be defined by a user via an input interface or be detected by algorithms.

The calibration unit of the electro-magnetic induction device according to the invention is configured (a) to control the electro-magnetic field adjustment mechanism to automatically vary the position of the electro-magnetic field generated by the coil design, (b) to receive an activation feedback signal from the sensor member upon detection of the activation of the target tissue, and (c) to control the electro-magnetic field adjustment mechanism to automatically stop variation of the position of the electro-magnetic field generated by the coil design when the activation feedback signal is received. Automatically stopping variation of the position and eventually field strength of the electro-magnetic field allows for a comparably quick and accurate provision of the electro-magnetic field for an efficient and secure activation of the target tissue. Also any unintended variation of the configuration of the electro-magnetic field after having found the appropriate position can be prevented. The field strength can also be referred to as magnitude of the electro-magnetic field.

The target tissue can be or comprise any muscle, muscular structure or section thereof which can be activated via the neural system. Particularly, it can be a diaphragm or midriff. The neural system can comprise or be a single or a plurality of nerves such as, particularly, the Phrenic nerve. Thereby, in many applications it is advantageous to repeatedly stimulate the neural system or the nerves and particularly the Phrenic nerve. The coil design of the electro-magnetic field generator allows to shape or customize the electro-magnetic field in compliance with the intended application of the device. In particular, the targeted shape can be created such that it is comparably sharp. This allows for specifically stimulating the neural system or a specific portion thereof. In particular, it allows for specifically stimulating a nerve such as the Phrenic nerve and for lowering or preventing or optimizing stimulation of other tissue such as other nerves or tissue neighboring, surrounding or overheading the targeted nerve. Thus, such co-stimulations need to be avoided whenever possible. This process of localizing the target nerve can also be supported by ultrasound imaging techniques. In order to stimulate one or both Phrenic nerves at a neck, coil design can be provided, which, e.g., can be characterized by a double coil generating a focal e-field area, multiple coils generating multiple focal e-field areas, a cone-shaped coil, a parabolic coil, a small circular coil or any curved or bulged coil, or any combination thereof.

The mounting arrangement can be embodied to hold the coil design of the electro-magnetic field generator in a specific target position at the human or animal body. In particular, such target position may be a position in which a targeted portion of the neural system can be reached by the electro-magnetic field created by the coils. The term "holding at" as used in connection with the mounting arrangement can relate to the coil design being in contact with the body or in close distance to it. The position and orientation of the coil design can thereby be predefined or distinct.

The term "in communication" as used in connection with the calibration unit can relate to any connection of elements allowing to communicate such as to transfer or exchange information or data. The elements can be in communication by being in wired or wireless connection with each other.

By configuring the calibration unit in accordance with the invention, the electro-magnetic field generator can automatically be orientated and adjusted, i.e. calibrated, such that the neural system is stimulated to specifically activate the target tissue. In particular, the strength of the electro-magnetic field created and the orientation of its targeted shape can be automatically varied until the neural system is stimulated such that the sensor receives a signal of the target tissue being activated. In that configuration, the neural system is specifically stimulated and due to the targeted shape of the electro-magnetic field the side effects such as stimulation of other portions of the neural system can be lowered or minimized. Moreover, the system could react to patient movements, and automatically re-orient towards the new location of the target nerve. Thereby, the calibration unit, the electro-magnetic field adjustment mechanism and the sensor member can form an automated feedback system implemented in the electro-magnetic induction device.

Like this, the electro-magnetic induction device according to the invention allows for an automatic, convenient and efficient operation and, more particular, for a simple, precise and specific localization of the portion of the neural system to be stimulated for activating the target tissue. By automatically calibrating the device, a considerable higher accuracy can be achieved compared to a manual localization of the relevant portion of the neural system, and usability can be improved. Additionally, the device allows for reducing the side effects in stimulation of the neural system.

Preferably, the mounting arrangement comprises a repositioning structure configured to automatically change a position of the coil design of the electro-magnetic field generator relative to the human or animal body when being held at the human or animal body. The term "position" as used in connection with the automatic changing by the repositioning structure can relate to a location, orientation, form-shaping or the like and combinations thereof. The position can be changed by tilting, shifting, relocating, reshaping or similar actions. Like this, the orientation of the electro-magnetic field can efficiently and precisely be adjusted.

Thereby, the electro-magnetic field adjustment mechanism preferably comprises the repositioning structure of the mounting arrangement and the calibration unit preferably is configured to automatically vary the position of the electro-magnetic field by inducing the repositioning structure to automatically change the position of the at least two electro-magnetic coils relative to the human or animal body. The repositioning structure of the mounting arrangement preferably comprises a tilting mechanism such as a joint configured to tilt the coil design of the electro-magnetic field generator relative to the human or animal body when being held at the human or animal body. This allows for an efficient adaptation of the position and/or orientation to adjust the electro-magnetic field in order to stimulate the neural system. Especially in the neck application with a longitudinally pertaining phrenic nerve, tilting a coil design having a peak, around a longitudinal axis at the neck surface in combination with varying the field strength/intensity allows all degrees of freedom necessary to locate the phrenic nerve. Besides a joint the tilting mechanism can be any suitable structure to tilt the coil design.

Alternatively or additionally, the electro-magnetic field generator preferably comprises a repositionable conductive element located in the electro-magnetic field generated by the coil design. Such a conductive element allows for an alternative efficient adjustment of the electro-magnetic field.

Thereby, the electro-magnetic field adjustment mechanism preferably comprises the conductive element of the electro-magnetic field generator and the calibration unit preferably is configured to automatically vary the position of the electro-magnetic field by inducing the electro-magnetic field adjustment mechanism to automatically reposition the conductive element in the electro-magnetic field. The conductive element preferably comprises a conductive shaft. Such a shaft may be a simple and efficient embodiments for precisely adjust the electro-magnetic field or its targeted shape. In this context the term "shaft" may relate to any suitable rod-like structure such as a bar, a pole, a stick, a stem, a post or the like.

Preferably, the electro-magnetic field generator comprises an array of coils including the coil design. In particular, the array can consist of three or more coils. Such array allows for more sophisticatedly shape and move the electro-magnetic field and particularly its targeted shape.

Thereby, the electro-magnetic field adjustment mechanism preferably comprises the array of coils of the electro-magnetic field generator and the calibration unit preferably is configured to automatically vary the position of the electro-magnetic field by inducing the electro-magnetic field adjustment mechanism to automatically empower different coil combinations of the array of coils. The coils of the array of coils preferably overlap. The array of coils of the electro-magnetic field generator preferably are arranged to generate a plurality of electro-magnetic fields each having a targeted shape, the array of coils being arranged such that the plurality of electro-magnetic fields overlap and generate an accumulated intensity. With such accumulated intensity, a more precise and well defined locally constrained, targeted electric field can be generated such that the neural system can be precisely stimulated.

Preferably, the sensor member comprises at least one electrode configured to be attached to the human or animal body such that it senses an activity of the target tissue. Such an electrode can efficiently detect activation of the target tissue such that the calibration process can stopped and/or a proper functioning of the activation can be monitored.

Additionally or alternatively, the sensor member preferably comprises a flow sensor having an adaptor connectable to a respiratory system of the human or animal body, the flow sensor being configured to detect an air flow change induced by an activity of the target tissue. The term "flow sensor" as used herein relates to any device allowing for detecting an air movement and, in particular, change of the air movement resulting in a pressure change. Typically, flow sensors measure the number of times a fixed volume is filled by the fluid within a specific time frame, a force or pressure produced in the flowing stream of the fluid or a velocity of the fluid over a known area. The adaptor can particularly be configured to be connected to an airway of the respiratory system. The flow sensor can be integral with the electro-magnetic induction device, e.g. in one unit. It can also be comprised in another unit such as an associated ventilation machine or the like.

Thereby, the adaptor of the flow sensor of the sensor member preferably is configured to be connected to a mouth and/or a nose of the human or animal body. The term "connected" as used herein relates to any direct connection or indirect connection via another element. For example, the adaptor can be indirectly connected to the mouth and/or nose via a tube.

Additionally or alternatively, the sensor member preferably comprises accelerators and/or gyroscopes and/or strain gauges, on the chest of the patient to detect diaphragm contractions. Also, an oesophagus catheter or other types of catheters may be used as a sensor member to detect activation of the diaphragm. A catheter to measure compound muscle action potentials (CMAP) of diaphragm may be used as a sensor member. A catheter in esophagus that measures the electrical activity of the diaphragm may be used as a sensor member. EMG measurement of diaphragm using catheter may be used. A transdiaphragmatic pressure sensor as catheter may be used as a sensor member, measuring gastric pressure (Pga) and esophagus pressure (Pes), sensor type: balloon catheter and pressure transducer, this requires the placement of small balloon-tipped catheters into the esophagus and stomach to assess intrathoracic and intra-abdominal pressures, respectively. Or, ultrasound monitoring may be used as a sensor member to detect diaphragm activations. Further, oxymetry measures may be used as indicators about inhalation activities/diaphragm activation. Also elastic bands/belts (around chest or other expanding structures) may be used as a sensor member to detect diaphragm activations; cross-section changes in bands/belts can serve as indicators for muscle/diaphragm contractions. Electrodes on target muscles/diaphragm to measure action potentials (e.g. electroenzephalograms) can be used as a sensor member to detect diaphragm activation. For example, cutaneous EMG measurement of diaphragm may be used as sensor member, whereby diaphragmatic EMG is monitored with a surface electrode positioned between the seventh and ninth intercostal spaces in the anterior axillary line. Mechanical stretch sensors on skin measuring thorax deformation may be used as a sensor member. Electrical impedance tomography, e.g. in form of a belt measuring lung volume, may be used as a sensor member.

Preferably, the mounting arrangement is configured to hold the coil design at the neck of the human or animal body such that a Phrenic nerve of the neural system of the human or animal body can be reached by the electro-magnetic field generated by the coil design of the electro-magnetic field generator. Such an embodiment allows for efficiently stimulating the Phrenic nerve and to activate the diaphragm.

Thereby, the mounting arrangement preferably comprises an arc member arrangable in distance around the neck of the human or animal body, the two coils of the electro-magnetic field generator being held at the arc member of the mounting arrangement. The coil design can be movable along the arc member. Or, the arc member can be equipped with the array of coils. Such arc member allows to provide a comparably high flexibility in relocating the coils and/or the electro-magnetic field. The arc member preferably is equipped with an access passage. The passage can be embodied as recess, slot, through hole or the like. Such passage allows the human or animal body to be accessed particularly in an area where the electro-magnetic field is applied. Like this, e.g., a catheter may be placed in a neck area where the Phrenic nerve is stimulated.

Preferably, the electro-magnetic induction device comprises a tracker configured to detect a movement of the human or animal body relative to the coil design of the electro-magnetic field generator and to automatically change the position of the electro-magnetic field to compensate the detected movement of the human or animal body relative to the coil design of the electro-magnetic field generator. Such arrangement allows to ensure a proper operation even in cases the body moves to certain extent.

Preferably, the electro-magnetic field adjustment mechanism is configured to automatically adjust a field strength of the electro-magnetic field generated by the coil design and the calibration unit is configured to control the electro-magnetic field adjustment mechanism to automatically vary the field strength of the electro-magnetic field generated by the coil design and to control the electro-magnetic field adjustment mechanism to automatically stop variation of the field strength of the electro-magnetic field generated by the coil design when the activation feedback is received. Such arrangement allows for efficiently adjust and dimension the electro-magnetic filed or its targeted shape in order to achieve a proper simulation.

Preferably, the electro-magnetic field adjustment mechanism is configured to automatically adjust temporal characteristics of the electro-magnetic field and the calibration unit is configured to control the electro-magnetic field adjustment mechanism to automatically vary the temporal characteristics of the electro-magnetic field and, optionally, to control the electro-magnetic field adjustment mechanism to automatically stop variation of the temporal characteristics of the electro-magnetic field generated by the coil design when the activation feedback is received.

Thereby, the electro-magnetic induction device preferably comprises an alarm unit, wherein the tracker is connected to the alarm unit and configured to activate the alarm unit when the detected movement exceeds a range of compensation achievable by changing the position of the electro-magnetic field generated by the two coils via the electro-magnetic field adjustment mechanism. The alarm can be an acoustic, a visual or a tactile signal, or any combination thereof.

Preferably, the electro-magnetic field generator is further configured to automatically adjust the transient field characteristics, e.g. pulse form, pulse duration, pulse frequency, intertrain-intervals, etc. of the electro-magnetic field generated by the coil design and the calibration unit is configured to control the electro-magnetic field adjustment mechanism to automatically vary the transient field characteristics of the electro-magnetic field generated by the coil design and to control the electro-magnetic field generator to automatically stop variation of the transient field characteristics of the electro-magnetic field generated by the coil design when the activation feedback is received.

Preferably, the sensor member comprises a pressure sensor having an adaptor connectable to a respiratory system of the human or animal body, the pressure sensor being configured to detect a pressure change induced by an activity of the target tissue. The adaptor of the pressure sensor of the sensor member can be configured to be connected to a mouth and/or a nose of the human or animal body. The pressure sensor can be integral with the electro-magnetic induction device, e.g. in one unit. It can also be comprised in another unit such as an associated ventilation machine or the like. Such an arrangement allows for detecting an activation of the target tissue resulting in a respiration of the patient.

The electro-magnetic induction device according to the invention and its preferred embodiments can advantageously be used for transcutaneous electro-magnetic induction of a Phrenic nerve for a diagnostic purpose to assess diaphragm function, or sleep apnoa, or other forms of sleep-disordered breathing.

Or, the electro-magnetic induction device according to the invention and its preferred embodiments can advantageously be used for repetitive regular transcutaneous electro-magnetic induction of a Phrenic nerve for therapeutic use in patients with no spontaneous breath, for example for reanimation and keeping alive patients who have no or impaired function of a respiratory center, e.g. sedated patients, intensive care patients or anaesthetized patients. The repetitive regular induction can be in particular ten to fifty stimuli per minute. The no function of the respiratory center can result from drugs or opioid consumption. The use can be involved in an immediate therapy for patients with missing stimulus due to interrupted connection between respiratory center and diaphragm such as, e.g., paraplegic patients after accidents, for use in patients with missing stimulus due to sedation or respiratory depression, or for use in mechanically ventilated patients without trigger.

The electro-magnetic induction device according to the invention and its preferred embodiments can also advantageously be used for repeated transcutanous electro-magnetic induction of a Phrenic nerve for therapeutic use in patients with no or insufficient spontaneous diaphragm contractions who have at least a partly intact Phrenic nerve. These therapeutic applications may include for example to treat or avoid diaphragm weakness in mechanically ventilated patients, to avoid or treat lung infections in mechanically ventilated patients, to avoid or treat lung injuries or other positive pressure related complications, for use in COPD patients, for reanimation and keeping alive patients who have impaired function of the respiratory center (e.g. from drugs or opeoids), for treatment of sleep apnoa and other forms of sleep-disordered breathing; to treat patients with idiopathic diaphragm paralysis, neuralgic amyotrophy or ALS, to treat hypercapnia. For these applications it may be useful to design the coil positioning mechanism in the following way: The patient lies on a pillow or mattress which adapts its shape to the patient's anatomy. This could be a vacuum pillow, wherein the patient head could be fixated in a position after vacuumization. The coils are fixed to a holder, which is mounted to the mattress or bed or which lies on the mattress underneath the vacuum pillow. An automated adjustment mechanism is included at the coil holder, to change the direction of the stimulation. The adjustment mechanism and coil construct may be surrounded by a cleanable or disposable cover, to protect the patient from mechanical coil movements and to protect the coil mechanism from decontamination.

Preferably, the calibration unit is configured (i) to control the electro-magnetic field generator to generate the electro-magnetic field in pulses while the position of the electro-magnetic field generated by the coil design is varied, and (ii) to control the electro-magnetic field generator to generate the electro-magnetic field as train when variation of the position of the electro-magnetic field generated by the coil design is stopped. By separating between the provision of pulses when adjusting the position of the electro-magnetic field and of a train stimulating the target tissue, an optimized activation of the target tissue can be achieved depending on its purpose. In particular, for having an appropriate position of the elector-magnetic field, the target tissue or a nerve associated to it has to be localized. For that purpose short pulses are sufficient and cause less discomfort to the patient. In contrast for stimulating the target tissue, e.g. a diaphragm to cause breathing, the train can be more efficient since contraction over an appropriate time can efficiently be achieved.

Thereby, the calibration unit preferably is configured to control the electro-magnetic field generator to generate the electro-magnetic field as train with an initially lower and then increasing field strength than the locally constrained, targeted electro-magnetic field in pulses. In particular, the field strength of the train can be initially slightly lower to avoid discomfort, then increased gradually until a desired intensity of the muscle contraction is reached and ultimately the field strength of the train can be higher than the field strength of the pulses. Like this, it can be assured that the target tissue is securely stimulated after the correct position of the electro-magnetic field is found.

Preferably, the activation feedback signal comprises plural responses of activation of the target tissue each associated to one specific position and eventually one specific field strength of the electro-magnetic field generated by the coil design, and the calibration unit is configured to control the electro-magnetic field adjustment mechanism to adjust the position and eventually field strength of the electro-magnetic field to the specific position associated to the most appropriate of the plural responses of the activation feedback signal or the most desirable signal characteristic, when the activation feedback signal is received. The term "most appropriate" as used herein can particularly relate to a strength of the response. In particular, the most appropriate response can be the strongest response. Additionally or alternatively, the most appropriate response can also be determined by other response properties. Like this, the best or most efficient position and eventually field strength of the electro-magnetic field can be determined and adjusted. In particular, by first gathering plural responses for plural positions and eventually field strengths and the selecting the strongest or most appropriate response, the configuration of the electro-magnetic filed can be optimized. The term "strong" in connection with the response can relate to a strength or intensity of activity of the target tissue. Such strength or intensity can correlate to the strength or intensity of the signal provided by the sensor member.

Preferably, the activation feedback signal comprises plural responses of activation of the target tissue each associated to one specific position of the target area of the electro-magnetic field generated by the coil design, and the calibration unit is configured to control the electro-magnetic field adjustment mechanism to adjust the position of the electro-magnetic field to the specific position associated to the most appropriate response characteristic of the plural responses of the activation feedback signal, when the activation feedback signal is received, and/or to adjust temporal field characteristics to the specific position and temporal settings associated to the most appropriate of the plural responses of the activation feedback signal, when the activation feedback signal is received, and/or to adjust the temporal field characteristics to the specific position and temporal settings associated to the most appropriate response characteristic of the plural responses of the activation feedback signal, when the activation feedback signal is received.

In another aspect, the invention is a process of manufacturing an electro-magnetic induction device for activating a target tissue in a human or animal body via its muscular or neural system. The process comprises: (i) assembling (i.a) an electro-magnetic field generator with coil design configured to generate a spatial electro-magnetic field having a targeted shape, (i.b) a mounting arrangement holding the coil design of the electro-magnetic field generator at the human or animal body, and (i.c) a sensor member configured to detect an activation of the target tissue, to the electro-magnetic induction device, (ii) assembling (ii.a) an electro-magnetic field adjustment mechanism configured to automatically adjust the position of the electro-magnetic field generated by the coil design, and (ii.b) a calibration unit in communication with the sensor member and with the electro-magnetic field adjustment mechanism, to the electro-magnetic induction device, and configuring the calibration unit (iii.a) to control the electro-magnetic field adjustment mechanism to automatically vary the position of the electro-magnetic field generated by the coil design, (iii.b) to receive an activation feedback signal from the sensor member upon detection of the activation of the target tissue, and (iii.c) to control the electro-magnetic field adjustment mechanism to automatically stop variation of the position of the electro-magnetic field generated by the coil design when the activation feedback is received.

The process according the invention allows for efficiently manufacturing the electro-magnetic induction device according to the invention as well as its preferred embodiments. Thereby, the effects and benefits described above in connection with the electro-magnetic induction device according to the invention can be achieved.

Preferably, the mounting arrangement is provided with a repositioning structure configured to automatically change a position of the coil design of the electro-magnetic field generator relative to the human or animal body when being held at the human or animal body. Thereby, the electro-magnetic field adjustment mechanism preferably is provided with the repositioning structure of the mounting arrangement and the calibration unit preferably is configured to automatically vary the position of the electro-magnetic field by inducing the repositioning structure to automatically change the position of the at least two electro-magnetic coils relative to the human or animal body. The repositioning structure of the mounting arrangement preferably is provided with a tilting mechanism such as a joint configured to tilt the coil design of the electro-magnetic field generator relative to the human or animal body when being held at the human or animal body.

Preferably, the electro-magnetic field generator is provided with a repositionable conductive element located in the electro-magnetic field generated by the coil design. Thereby, the electro-magnetic field adjustment mechanism preferably is provided with the conductive element of the electro-magnetic field generator and the calibration unit preferably is configured to automatically vary the position of the electro-magnetic field by inducing the electro-magnetic field adjustment mechanism to automatically reposition the conductive element in the electro-magnetic field. The conductive element preferably is provided with a conductive shaft.

Preferably, the electro-magnetic field generator is provided with an array of coils including the coil design. Thereby, the electro-magnetic field adjustment mechanism preferably is provided with the array of coils of the electro-magnetic field generator and the calibration unit preferably is configured to automatically vary the position of the electro-magnetic field by inducing the electro-magnetic field adjustment mechanism to automatically empower different coil combinations of the array of coils. Coils of the array of coils preferably overlap. The array of coils of the electro-magnetic field generator preferably are arranged to generate a plurality of spatial electro-magnetic fields each having a targeted shape, the array of coils being arranged such that the plurality of electro-magnetic fields overlap and generate an accumulated intensity.

Preferably, the sensor member is provided with at least one electrode configured to be attached to the human or animal body such that it senses an activity of the target tissue.

Preferably, the sensor member is provided with a flow sensor having an adaptor connectable to a respiratory system of the human or animal body, the flow sensor being configured to detect an air flow change induced by an activity of the target tissue. Thereby, the adaptor of the flow sensor of the sensor member preferably is configured to be connected to a mouth and/or a nose of the human or animal body.

Preferably, the mounting arrangement is configured to hold the coil design at the neck of the human or animal body such that a Phrenic nerve of the neural system of the human or animal body can be reached by the electro-magnetic field generated by the coil design of the electro-magnetic field generator. Thereby, the mounting arrangement preferably is provided with an arc member arrangable in distance around the neck of the human or animal body, the two coils of the electro-magnetic field generator being held at the arc member of the mounting arrangement. The arc member preferably is equipped with an access passage.

Preferably, the process further comprises a step of assembling a tracker into the electro-magnetic induction device, wherein the tracker is configured to detect a movement of the human or animal body relative to the coil design of the electro-magnetic field generator and to automatically change the position of the electro-magnetic field to compensate the detected movement of the human or animal body relative to the coil design of the electro-magnetic field generator.

Preferably, the electro-magnetic field adjustment mechanism is configured to automatically adjust a field strength of the electro-magnetic field generated by the coil design and the calibration unit is configured to control the electro-magnetic field adjustment mechanism to automatically vary the field strength of the electro-magnetic field generated by the coil design and to control the electro-magnetic field adjustment mechanism to automatically stop variation of the field strength of the electro-magnetic field generated by the coil design when the activation feedback is received.

Thereby, the process preferably comprises: assembling an alarm unit into the electro-magnetic induction device, wherein the tracker is connected to the alarm unit and configured to activate the alarm unit when the detected movement exceeds a range of compensation achievable by changing the position of the electro-magnetic field generated by the two coils via the electro-magnetic field adjustment mechanism. The alarm can be an acoustic, a visual or a tactile signal, or any combination thereof.

Preferably, the process comprises a step of configuring the calibration unit (i) to control the electro-magnetic field generator to generate the electro-magnetic field in pulses while the position of the electro-magnetic field generated by the coil design is varied, and (ii) to control the electro-magnetic field generator to generate the electro-magnetic field as train when variation of the position of the electro-magnetic field generated by the coil design is stopped.

Thereby, the process preferably comprises a step of configuring the calibration unit to control the electro-magnetic field generator to generate the electro-magnetic field as train with an initially lower and the increasing field strength than the electro-magnetic field in pulses.

Preferably, the activation feedback signal comprises plural responses of activation of the target tissue each associated to one specific position of the electro-magnetic field generated by the coil design, and the calibration unit is configured to control the electro-magnetic field adjustment mechanism to adjust the position of the electro-magnetic field to the specific position associated to the strongest or most appropriate of the plural responses of the activation feedback signal, when the activation feedback signal is received, and/or to adjust temporal field characteristics to the specific position and temporal settings associated to a most appropriate of the plural responses of the activation feedback signal, when the activation feedback signal is received, and/or to adjust the temporal field characteristics to the specific position and temporal settings associated to the most appropriate response characteristic of the plural responses of the activation feedback signal, when the activation feedback signal is received.

Preferably, the activation feedback signal comprises plural responses of activation of the target tissue each associated to one specific position of the target area of the electro-magnetic field generated by the coil design, comprising configuring the calibration unit to control the electro-magnetic field adjustment mechanism to adjust the position of the electro-magnetic field to the specific position associated to the most appropriate response characteristic of the plural responses of the activation feedback signal, when the activation feedback signal is received.

Preferably, the process comprises configuring the electro-magnetic field adjustment mechanism to automatically adjust temporal characteristics of the electro-magnetic field and configuring the calibration unit to control the electro-magnetic field adjustment mechanism to automatically vary the temporal characteristics of the electro-magnetic field and, optionally, to control the electro-magnetic field adjustment mechanism to automatically stop variation of the temporal characteristics of the electro-magnetic field generated by the coil design when the activation feedback is received.

In a further other aspect, the invention is a method of activating a target tissue in a human or animal body via its muscular or neural system, comprising: (i) positioning coil design at the human or animal body, (ii) generating a spatial electro-magnetic field having a targeted shape by means of the coil design, (iii) sensing for activation of the target tissue, (iv) adjusting a position of the electro-magnetic field generated by the coil design, (v) automatically varying the position of the electro-magnetic field generated by the coil design, (vi) evaluating an activation feedback obtained by the sensing for activation of the target tissue, and (vii) automatically stopping variation of the position of the electro-magnetic field generated by the coil design when an activation is detected by the sensing for activation of the target tissue.

Such method allows for efficiently activating the target tissue. This can, e.g., be beneficial for preventing any defects resulting from the disuse of the target tissue. Particularly, when used in a ventilation application such method can prevent disfunctioning of the diaphragm resulting from not using it during ventilation. More specifically, the method according to the invention allows for achieving the effects and benefits described above in connection with the electro-magnetic induction device according to the invention.

Thereby, automatically varying the position of the electro-magnetic field preferably comprises automatically changing the position of the at least two electro-magnetic coils relative to the human or animal body. Automatically varying the position of the electro-magnetic field preferably comprises automatically repositioning a conductive element in the electro-magnetic field.

Preferably, the electro-magnetic field generator comprises an array of coils including the coil design. Thereby, automatically varying the position of the electro-magnetic field comprises automatically empowering different coil combinations of the array of coils. Coils of the array of coils preferably overlap. The array of coils of the electro-magnetic field generator preferably are arranged to generate a plurality of electro-magnetic fields each having a locally constrained, targeted electric field, the array of coils being arranged such that the plurality of electro-magnetic fields overlap and generate an accumulated intensity.

Preferably, sensing for activation of the target tissue comprises attaching at least one electrode to the human or animal body.

Preferably, sensing for activation of the target tissue comprises connecting a flow sensor to a respiratory system of the human or animal body, and detecting an air flow change induced by an activity of the target tissue. Thereby, the flow sensor preferably is connected to a mouth and/or a nose of the human or animal body.

Preferably, positioning the coil design at the human or animal body comprises holding the coil design at a neck of the human or animal body such that a Phrenic nerve of the neural system of the human or animal body can be reached by the electro-magnetic field generated by the coil design. Advantageously, there are both sides of the neck involved in activating the diaphragm. In particular, two electro-magnetic induction devices can be placed in parallel at the neck such that the Phrenic nerves can be stimulated on both sides. Preferably, these two devices are coupled to cooperate in a synchronized or matched manner.

Preferably, the method comprises automatically adjusting a field strength of the electro-magnetic field generated by the coil design, automatically varying the field strength of the electro-magnetic field generated by the coil design and stopping variation of the field strength of the electro-magnetic field generated by the coil design when an activation of the target tissue is sensed.

Preferably, the method comprises generating the electro-magnetic field in pulses while the position of the electro-magnetic field generated by the coil design is varied, and generating the electro-magnetic field as train when variation of the position of the target area of the electro-magnetic field generated by the coil design is stopped.

Thereby, the method preferably comprises generating the electro-magnetic field as train with an initially lower and then increasing field strength than the electro-magnetic field in pulses.

Preferably, the activation feedback signal comprises plural responses of activation of the target tissue each associated to one specific position of the electro-magnetic field generated by the coil design, and the position of the electro-magnetic field is adjusted to the specific position associated to the strongest or most appropriate of the plural responses of the activation feedback signal, when the activation feedback signal is received.

The electro-magnetic field generator of all embodiments described herein advantageously is configured to provide pulses of electromagnetic fields, with adjustable field strength and frequency. Like this, sudden convulsion of the patient or of specific body parts can be prevented. This can increase convenience and efficiency of the stimulation.

Preferably, the activation feedback signal comprises plural responses of activation of the target tissue each associated to one specific position of the target area of the electro-magnetic field generated by the coil design, and the position of the electro-magnetic field is adjusted to the specific position associated to the most appropriate response characteristic of the plural responses of the activation feedback signal, when the activation feedback signal is received, and/or to adjust temporal field characteristics to the specific position and temporal settings associated to the most appropriate of the plural responses of the activation feedback signal, when the activation feedback signal is received, and/or to adjust the temporal field characteristics to the specific position and temporal settings associated to the most appropriate response characteristic of the plural responses of the activation feedback signal, when the activation feedback signal is received.

Preferably, the method comprises adjusting temporal characteristics of the electro-magnetic field and varying the temporal characteristics of the electro-magnetic field and, optionally, stopping variation of the temporal characteristics of the electro-magnetic field generated by the coil design when the activation feedback is received.

BRIEF DESCRIPTION OF THE DRAWINGS

The electro-magnetic induction device according to the invention as well as the process and method according to the invention are described in more detail hereinbelow by way of exemplary embodiments and with reference to the attached drawings, in which:

FIG. 11 shows a flow scheme of a second embodiment of a method of activating a target tissue in a human or animal body via its muscular or neural system according to the invention; and FIG. 12 shows a flow scheme of a third embodiment of a method of activating a target tissue in a human or animal body via its muscular or neural system according to the invention.

DESCRIPTION OF EMBODIMENTS

In the following description certain terms are used for reasons of convenience and are not intended to limit the invention. The terms "right", "left", "up", "down", "under" and "above" refer to directions in the figures. The terminology comprises the explicitly mentioned terms as well as their derivations and terms with a similar meaning. Also, spatially relative terms, such as "beneath", "below", "lower", "above", "upper", "proximal", "distal", and the like, may be used to describe one element's or feature's relationship to another element or feature as illustrated in the figures. These spatially relative terms are intended to encompass different positions and orientations of the devices in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. The devices may be otherwise oriented (rotated 90 degrees or at other orientations), and the spatially relative descriptors used herein interpreted accordingly. Likewise, descriptions of movement along and around various axes include various special device positions and orientations.

To avoid repetition in the figures and the descriptions of the various aspects and illustrative embodiments, it should be understood that many features are common to many aspects and embodiments. Omission of an aspect from a description or figure does not imply that the aspect is missing from embodiments that incorporate that aspect. Instead, the aspect may have been omitted for clarity and to avoid prolix description. In this context, the following applies to the rest of this description: If, in order to clarify the drawings, a figure contains reference signs which are not explained in the directly associated part of the description, then it is referred to previous or following description sections. Further, for reason of lucidity, if in a drawing not all features of a part are provided with reference signs it is referred to other drawings showing the same part. Like numbers in two or more figures represent the same or similar elements.

Figure 1:
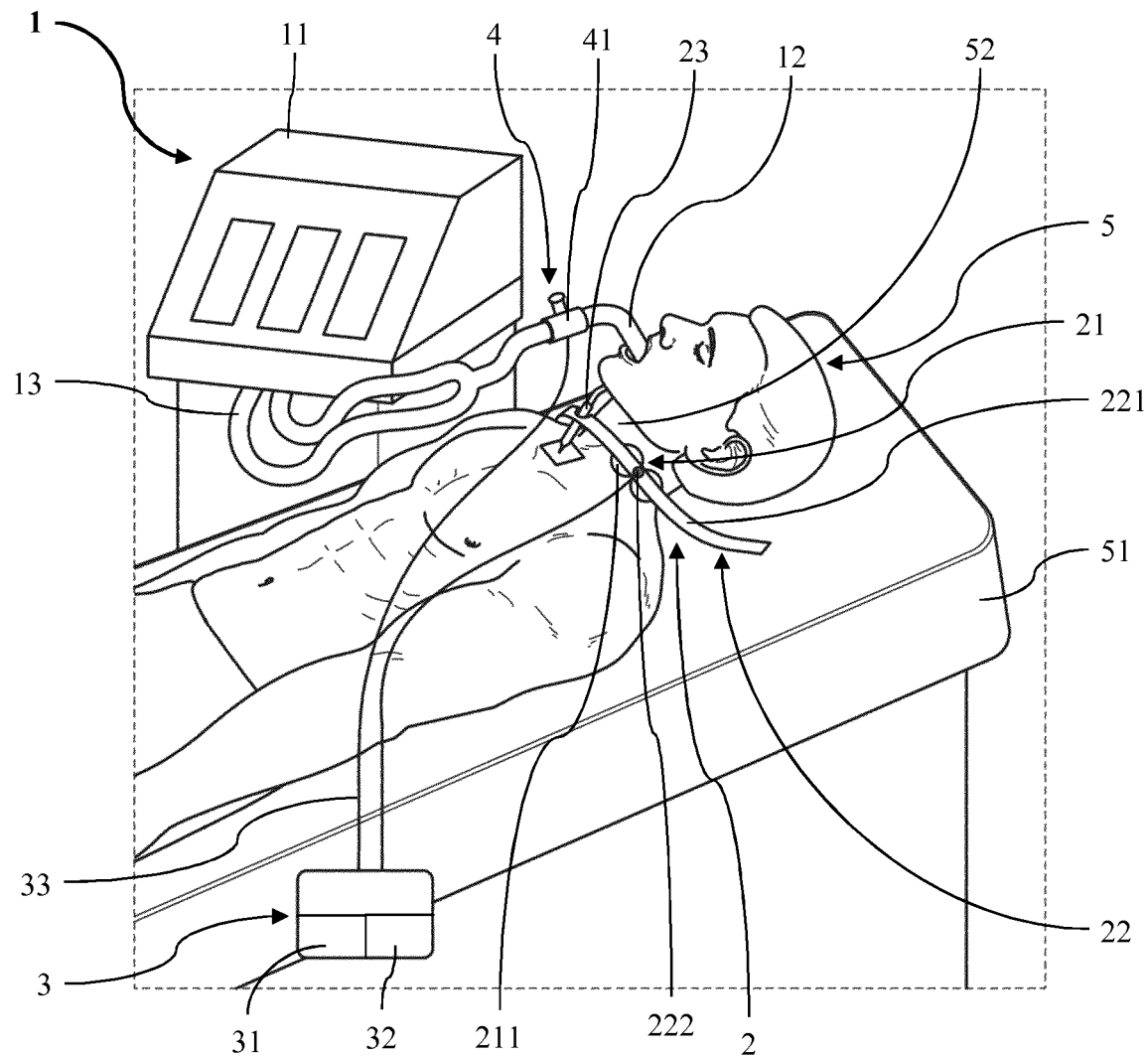
FIG. 1 shows a first implementation of a ventilation machine having a first embodiment of an electro-magnetic induction device according to the invention.
Figure 3:
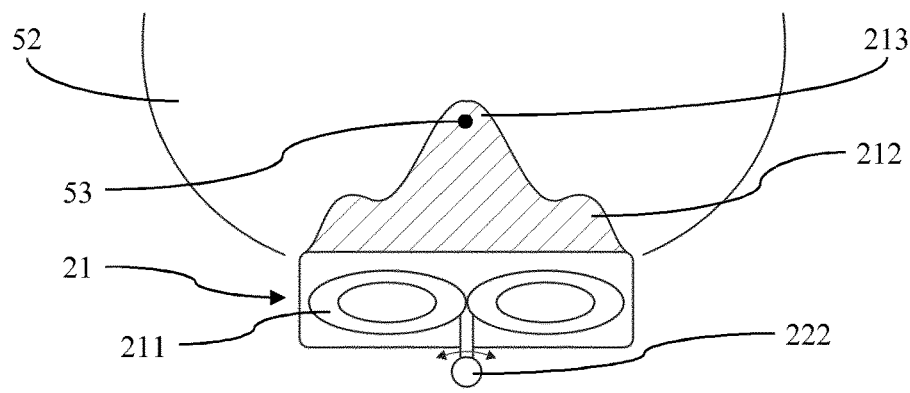
FIG. 3 shows a spatial electro-magnetic field generated by the electro-magnetic induction device of FIG. 1.

FIG. 1 shows a first implementation of a ventilation machine 1 having a first embodiment of an electro-magnetic induction device 2 (in the following also referred to as EMI device) according to the invention. The EMI device 2 comprises an electro-magnetic field generator 21 with two coils 211 as coil design. The coils 211 are located in one common plane and configured to generate a spatial electro-magnetic field 212. As can particularly be seen in FIG. 3, when operated, the two coils 211 generate the electro-magnetic field 212 towards a neck 52 of a patient 5. The electro-magnetic field 212 has a central targeted shape with a focality area 213 at which the electro-magnetic field 212 maximally extends into the neck 52.

Turning back to FIG. 1, the EMI device 2 has a mounting arrangement 22 with a neck arc 221 arranged at the neck 52 of the patient 5 and fixed to a bed 51 the patient 5 lies on. The neck arc 221 is equipped with a joint 222 as repositioning structure of an electro-magnetic field adjustment mechanism of the EMI device 2. The joint 222 holds the coils 211 at the neck 52 of the patient 5.

The ventilation machine 1 further comprises a ventilator 11 as air flow generator from which ventilation tubes 13 extend. The EMI device 2 has a mouthpiece 12 as adapter, i.e. as conduit interface of the ventilation machine 1. The mouthpiece 12 is applied to a mouth as entry point into the respiratory system of the patient 5. The ventilation tubes 13 are coupled to a flow sensor 41 of a sensor member 4 of the EMI device 2.

The EMI device 2 further has a controller 3 as processing unit with a calibration unit 31 and a field adjustment unit 32 of the electro-magnetic field adjustment mechanism. The controller 3 is in communication with the flow sensor 41 and the joint 222 via respective wires 33.

The calibration unit 31 is configured to manipulate the joint 222 to automatically vary the position of the focality area 213 of the electro-magnetic field 212 generated by the coils 211 and the controller 3 to vary the field strength of the electro-magnetic field 212. The aim of varying field strength and position of the electro-magnetic field 212 is to adjust the electro-magnetic field 212 such that it specifically stimulates a Phrenic nerve 53 of the patient 5 as can be best seen in FIG. 3. Upon stimulation of the Phrenic nerve 53, a diaphragm of the patient 5 is activated. Thereby, an airflow or breathing is induced which is sensed by the flow sensor 41.

The calibration unit 31 is configured to receive an activation feedback signal from the flow sensor 41 upon detection of activation of the diaphragm or upon detection of the airflow. Further, it is configured to stop variation of the position of the focality area 213 of the electro-magnetic field 212 and the controller 3 to stop variation of the field strength of the electro-magnetic field 212 when the activation feedback is received.

The ventilator 11 is configured to deliver air through the mouthpiece 12 into the respiratory system of the patient 5. Thereby, the controller 3 is configured to control the ventilator 11 to deliver air into the respiratory system according to a breathing scheme defined in the controller 3. In particular, the controller 3 regulates the activation of the diaphragm in coordination with the breathing scheme such that activation of the diaphragm via the Phrenic nerve 53 is coordinated with the ventilation of the patient 5.

Figure 2:
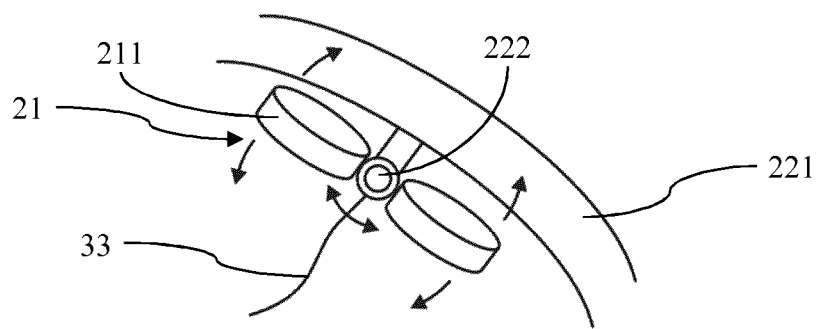
FIG. 2 shows an electro-magnetic field generator of the electro-magnetic induction device of FIG. 1.

In FIG. 2 the coils 211 of the electro-magnetic field generator 21 are shown on more detail. Thereby, it can be seen that the coils 211 are connected to the neck arc 221 via the joint 222. As indicated by the arrows in FIG. 2, the joint 222 can be tilted via the control unit 31 such that also the coils 211 are commonly tilted or rotated. During calibration of the EMI device 2 the calibration unit 31 automatically tilts the coils 211 relative to the neck 52 of the patient 5 by moving the joint 222. Thereby, the electromagnetic field 212 and particularly the focality area 213 of its targeted shape is moved correspondingly. In addition to that, the calibration unit 31 varies the field strength of the electro-magnetic field 212 until the Phrenic nerve is in within the focality area 213 and thereby stimulated.

The EMI device 2 is further equipped with a tracker 23 which is configured to detect a movement of the patient 5 relative to the coils 211 and to automatically induce a change of the position of the electro-magnetic field 212 to compensate the detected movement of the patient 5. The tracker 23 is in communication with an alarm unit. It activates the alarm unit when the detected movement exceeds a range of compensation achievable by changing the position of the electro-magnetic field 212.

The controller 3 is equipped with a wireless adapter to be connected to a mobile device such as a smartphone, tablet or the like as input interface. When the mobile device is connected, an operator can input an appropriate cyclic breathing scheme suitable for treating the patient 5. The breathing scheme is embodied such that the controller 3 induces operation in a predefined patient specific manner. Thereby, the ventilator 11 delivers air through the mouthpiece 12 into the respiratory system of the patient 5 by applying cycles of forwarding air into the respiratory system of the patient 5 and withdrawing air from the respiratory system in accordance with the breathing scheme. Further, the EMI device 2 activates the diaphragm right before each start of one of the cycles of the breathing scheme.

Figure 4:
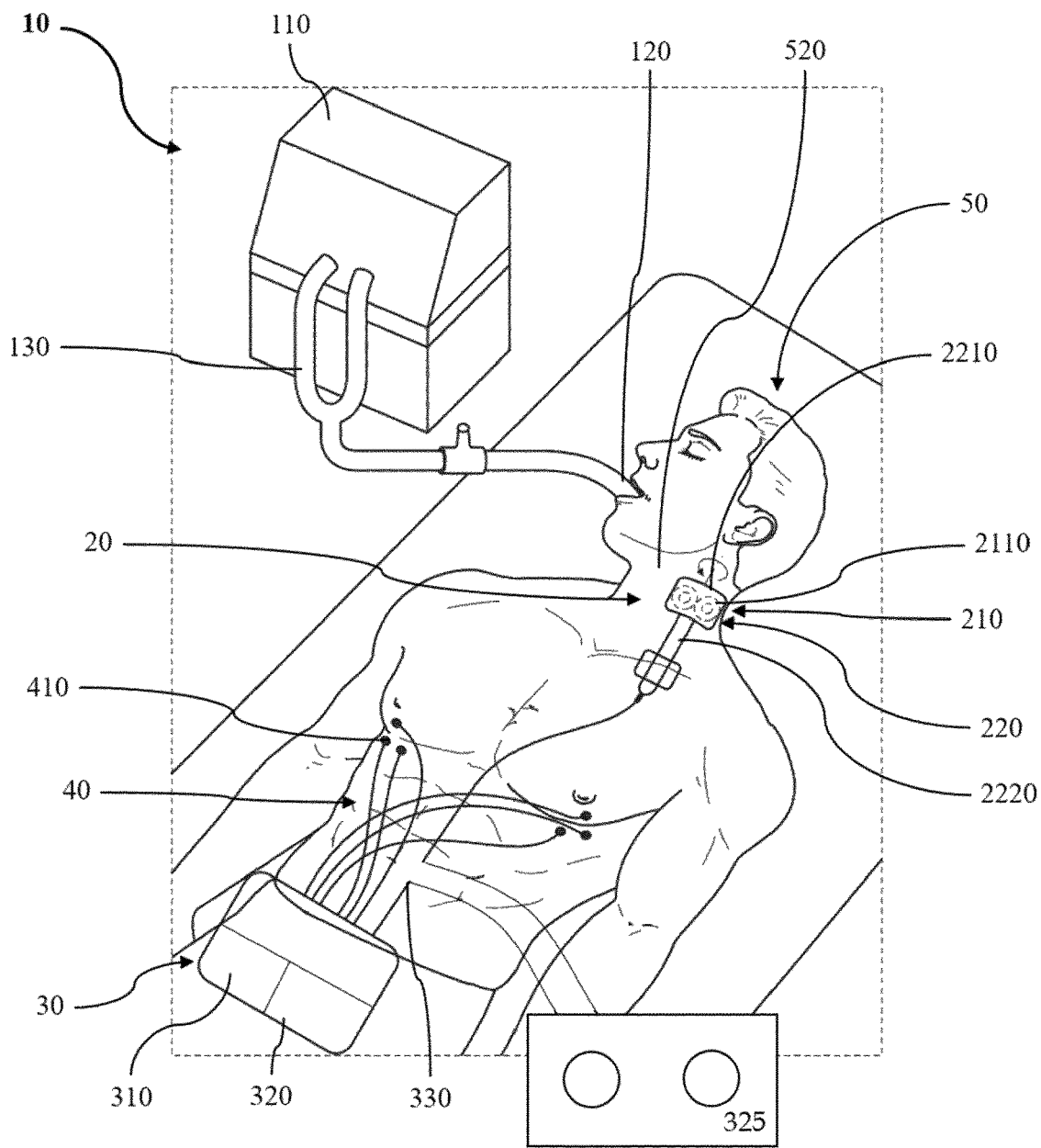
FIG. 4 shows a second implementation of a ventilation machine having a second embodiment of an electro-magnetic induction device according to the invention.

FIG. 4 shows a second implementation of a ventilation machine 10 having a second embodiment of an EMI device 20 according to the invention. The EMI device 20 comprises an electro-magnetic field generator 210 with two coils 2110. The coils 2110 are configured to generate a spatial electro-magnetic field with a targeted shape. The EMI device 20 further has a mounting arrangement 220 with a tape 2210. The tape 2210 is provided with an adhesive and attached to a neck 520 of a patient 50.

The EMI device 20 is equipped with a shaft 2220 as repositionable element extending towards the coils 2110 and can tilt the electro-magnetic field around an axis of the shaft.

The ventilation machine 10 comprises a ventilator 110 as air flow generator from which ventilation tubes 130 extend. The EMI device 20 has a mouthpiece 120 as adapter or as conduit interface of the ventilation machine 10. The mouthpiece 120 is applied to a mouth as entry point into the respiratory system of the patient 50.

The EMI device 20 has a controller 30 as a processing unit with a calibration unit 310 and a field adjustment unit 320 of the electro-magnetic field adjustment mechanism. On the body of the patient 50 a plurality of electrodes 410 comprised by a sensor member 40 for detecting activation of the diaphragm. The controller 30 is in communication with the electrodes 410 and magnetic stimulator 325 which connects to the shaft 2220 via respective wires 330.

The calibration unit 310 is configured to automatically vary the position of the electro-magnetic field by automatically inducing the field adjustment unit 320 to reposition the shaft 2220 and by automatically varying the electro-magnetic field strength. In particular, the shaft 2220 influences the alignment of the electromagnetic field around the axis of the shaft and thereby the location of the target area. Thus, by moving the shaft 2220, the electromagnetic field can be relocated. Like this, the electro-magnetic field can be moved within the neck 520 of the patient 50. In particular, the calibration unit 310 is configured to vary the position of the electro-magnetic field and to vary the field strength of the electro-magnetic field. Like this, the electro-magnetic field can be adjusted such that it specifically stimulates a Phrenic nerve of the patient 50. Upon stimulation of the Phrenic nerve, a diaphragm of the patient 50 is activated which is sensed by the electrodes 410.

The calibration unit 310 is configured to receive an activation feedback signal from the electrodes 410 upon detection of activation of the diaphragm. Further, it is configured to stop variation of the position of the electro-magnetic field and to control the controller 30 to stop variation of the field strength of the electro-magnetic field when the activation feedback is received. The ventilator 110 is configured to deliver air through the mouthpiece 120 into the respiratory system of the patient 50. The controller 30 is configured to control the ventilator 110 such that its delivery of air into the respiratory system is in line with a breathing scheme defined in the controller 30. In particular, the controller 30 regulates the activation of the diaphragm in coordination with the breathing scheme such that activation of the diaphragm via the Phrenic nerve is coordinated with the ventilation and breathing of the patient 50.

The controller 30 is equipped with a wireless adapter to be connected to a mobile device such as a smartphone, tablet or the like as input interface. When the mobile device is connected, an operator can input an appropriate cyclic breathing scheme suitable for treating the patient 50. The breathing scheme is embodied such that the controller 30 induces ventilation and Phrenic nerve stimulation in a predefined and patient specific manner. Thereby, the ventilator 110 delivers air through the mouthpiece 120 into the respiratory system of the patient 50 by applying cycles of forwarding air into the respiratory system of the patient 50 and withdrawing air from the respiratory system in accordance with the breathing scheme. Further, the EMI device 20 activates the diaphragm right before each start of one of the cycles of the breathing scheme.

Figure 5:
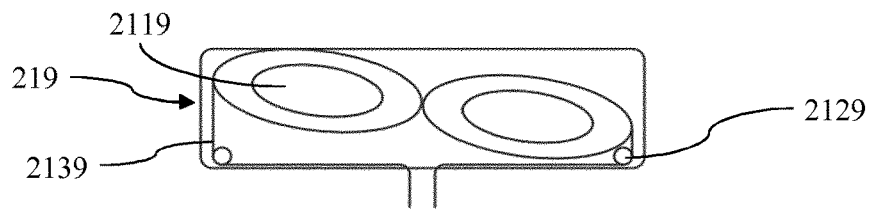
FIG. 5 shows an electro-magnetic field generator of a third embodiment of an electro-magnetic induction device according to the invention in a tilted state.

In FIG. 5 an electro-magnetic field generator 219 of a third embodiment of an EMI device according to the invention is shown. The electro-magnetic field generator 219 comprises a housing in which two coils 2119 are positioned. The coils 2119 are fixed to each other such that they can be moved or manipulated together as one unit. The coils 2119 are connected to cables 2139 at their lateral end sides. Starting from the coils 2119, the cables 2139 are redirected by respective pulleys 2129 and guided through an opening out of the housing.

Figure 6:
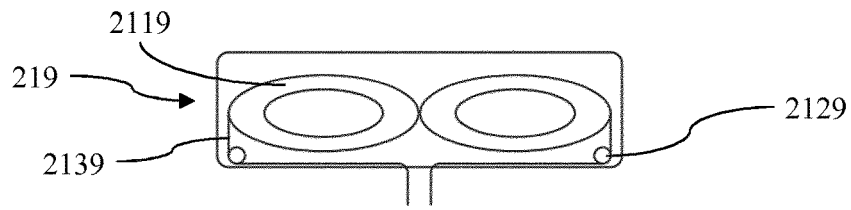
FIG. 6 shows the electro-magnetic field generator of FIG. 5 in a non-tilted state.

In FIG. 5 the coils 2119 are depicted in a tilted state in which the left coil 2119 is higher than the right coil 2119. For changing the tilting of the coils 2119, one of the cables 2139 can be pulled. As can be seen in FIG. 6, for moving the coils 2119 back to a straight position, the left cable 2139 is pulled such that the coils 2119 are rotated counter-clockwise.

Figure 7:
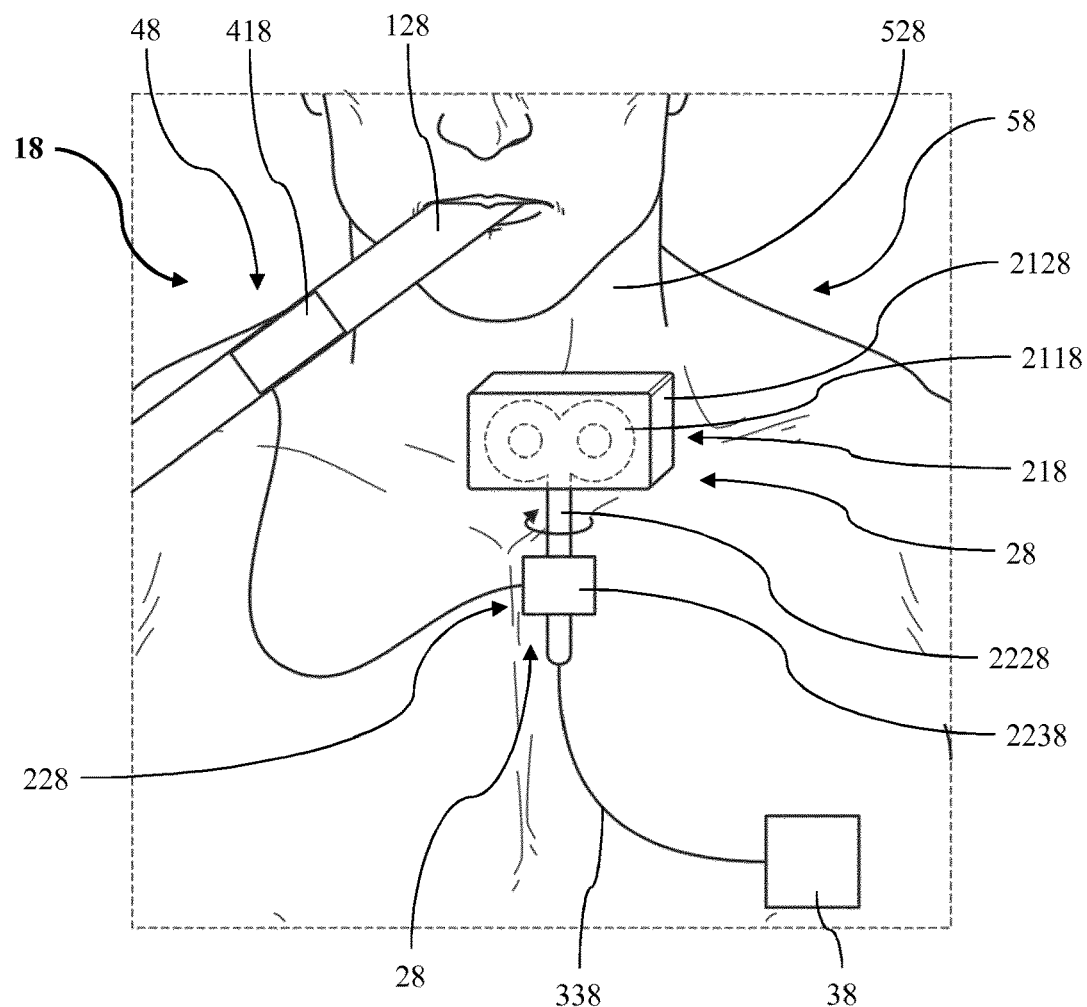
FIG. 7 shows a third implementation of a ventilation machine having a fourth embodiment of an electro-magnetic induction device according to the invention

FIG. 7 shows a third implementation of a ventilation machine 18 having a fourth embodiment of an EMI device 28 according to the invention. The EMI device 28 comprises an electro-magnetic field generator 218 with two coils 2118 as coil design. The electro-magnetic field generator 218 has a housing 2128 into which a shaft 2228 of a mounting arrangement 228 extends. The shaft 2228 is coupled to a shaft drive 2238 by which the shaft 2238 can be moved in the electro-magnetic field once created by the coils 2118.

The ventilation machine 18 comprises a ventilator from which ventilation tubes are connected to a mouthpiece 128 as adaptor or as conduit interface of the ventilation machine 18 via a flow sensor 418 of a sensor member 48. The mouthpiece 128 is applied to a mouth of a patient 58 as entry point into his respiratory system.

The EMI device 28 has a controller 38 as a processing unit with a calibration unit and a field adjustment unit. The housing 2128 of the electro-magnetic field generator 218 the shaft drive 2238 and the controller 38 are attached to the patient 58 and, particularly, the electro-magnetic field generator 218 to his neck 528. Thereby, an adhesive of the mounting arrangement 228 is used. The controller 38 is in communication with the flow sensor 418 and the shaft drive 2238 by means of wires 338.

The ventilation apparatus 18 is correspondingly operated as the ventilation apparatus 10 described above in connection with FIG. 4.

Figure 8:
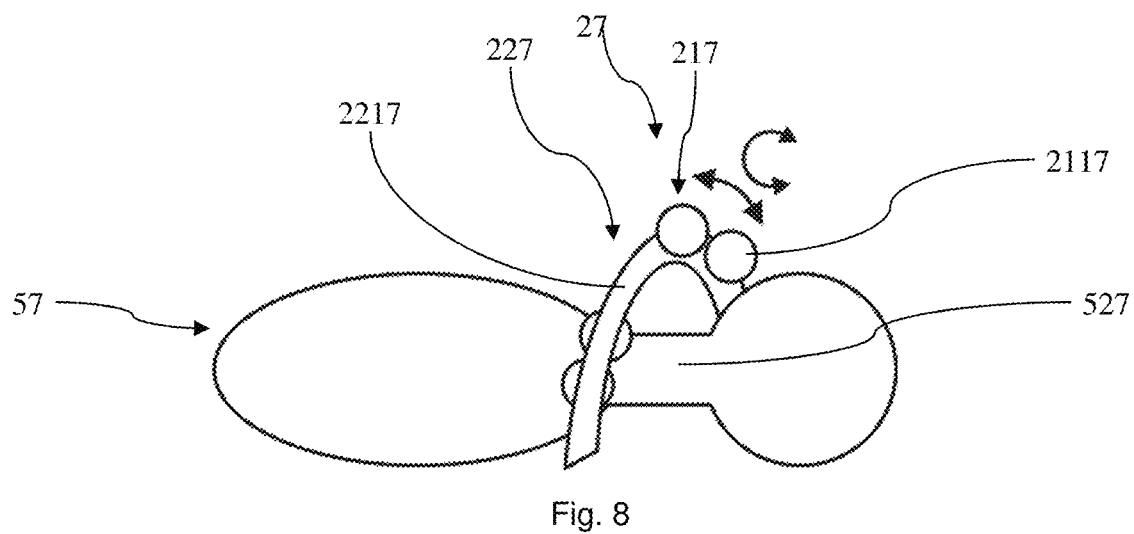
FIG. 8 shows a fifth embodiment of an electro-magnetic induction device according to the invention.

In FIG. 8 components of a fifth embodiment of an EMI device 27 according to the invention is shown. The EMI device 27 is similarly embodied as the EMI devices described above in connection with the previous Figures. However, a mounting arrangement 227 comprises an arc member 2217 to which coils 2117 of an electro-magnetic field generator 217 are mounted as coil design. The arc member 2217 is positioned around a neck 527 of a patient 57. The coils 2117 can be moved along the arc member 2217 and thereby around the neck 527 of the patient 57. Additionally, the coils 2117 can turn about the arc member 2217. By these movements of the coils 2117 a spatial electro-magnetic field and, in particular, a targeted shape thereof can be moved around and in the neck 527 for finding and stimulating a Phrenic nerve of the patient 57.

Figure 9:
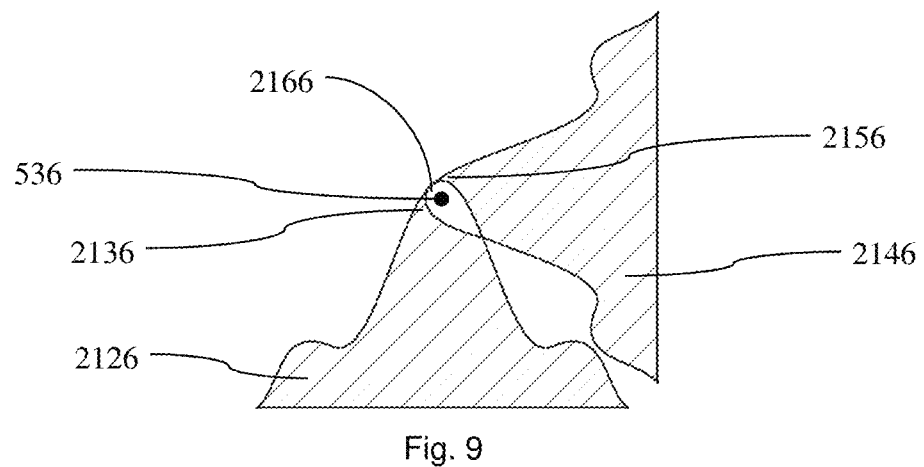
FIG. 9 shows a spatial electro-magnetic field generated by a sixth embodiment of an electro-magnetic induction device according to the invention.

FIG. 9 shows electromagnetic fields generated by coils of an electro-magnetic field generator of a sixth embodiment of an EMI device according to the invention. In particular, the electro-magnetic field generator comprises two pairs of coils wherein the pairs are perpendicular to each other. Thus, a first pair of coils generates a first electro-magnetic field 2126 having a targeted shape with a first focality area 2136. The second pair of coils generates a second electro-magnetic field 2146 having a targeted shape with a second focality area 2156. Since the coils of the first pair are perpendicular to the coils of the second pair, the first electro-magnetic field and the second electro-magnetic field overlap at their respective focality areas 2136, 2156. Like this, an area of accumulated intensity 2166 is created where the focality areas 2136, 2156 overlap. A Phrenic nerve 536 is positioned in the area of accumulated intensity 2166.

Figure 10:
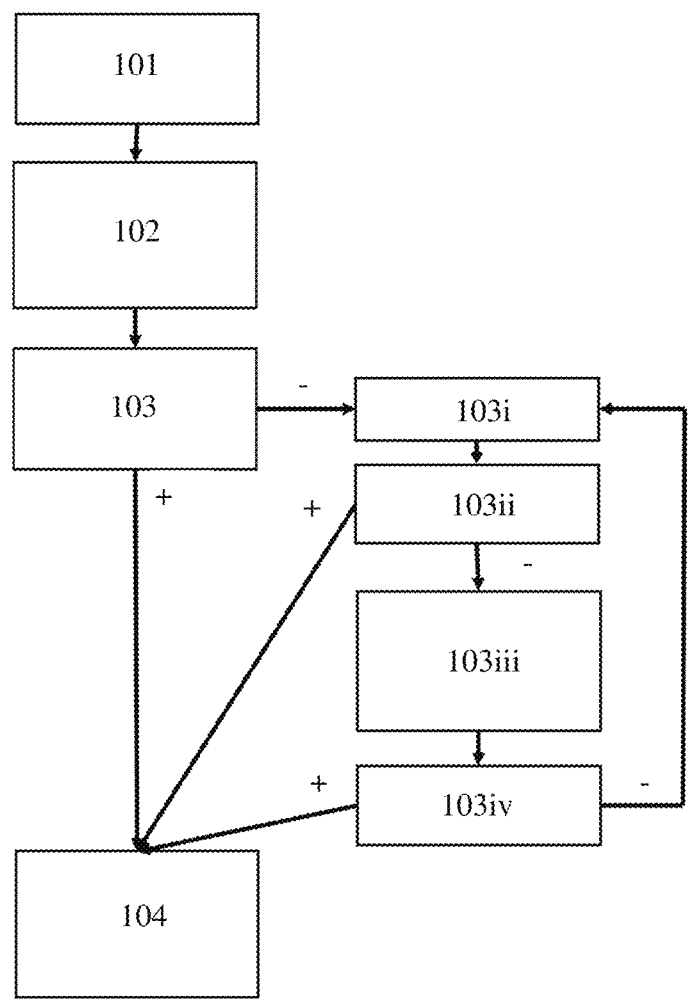
FIG. 10 shows a flow scheme of a first embodiment of a method of activating a target tissue in a human or animal body via its muscular or neural system according to the invention.
Figure 13:
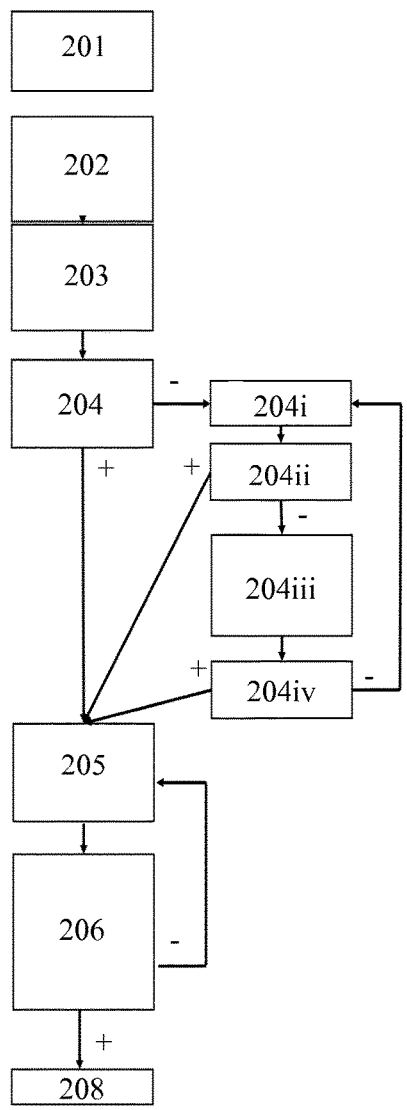
Figure 14:
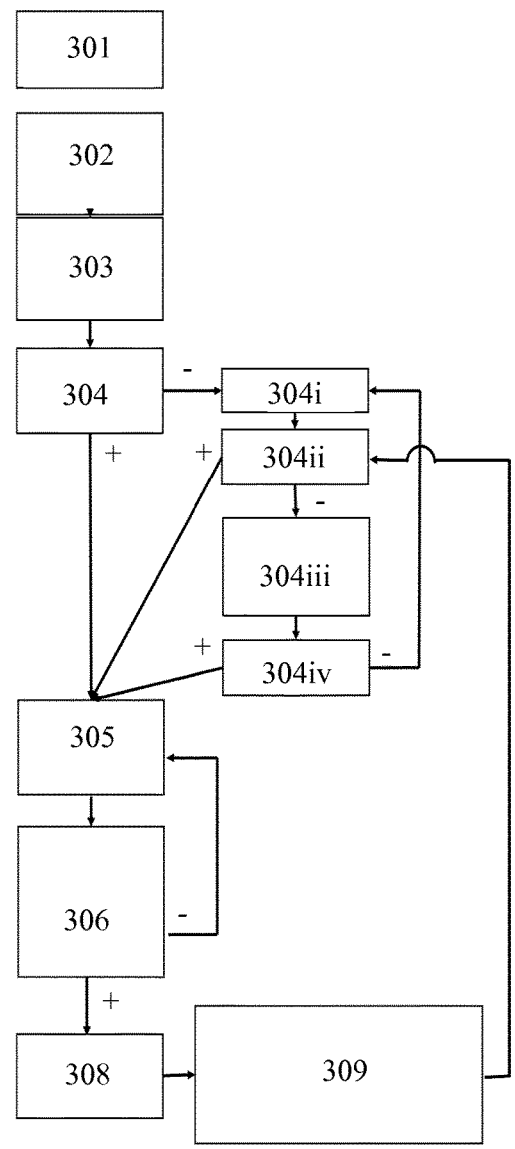

FIG. 10 shows a first embodiment of a method of activating a target tissue in a human or animal body via its muscular or neural system according to the invention. The first method can, e.g., be performed by using the electro-magnetic induction device 2 shown in FIG. 1.

In a first step 101, coils are positioned at the human or animal body close to a target nerve. For example the coils can be positioned at a neck in order to be close to a Phrenic nerve. In a second step 102, a spatial electro-magnetic field having a targeted shape is generated by means of the coils. In a third step 103, it is sensed if the target tissue associated to the target nerve is activated. If this is the case, in a fourth step 104, the position of the coils and the intensity of the electro-magnetic field are frozen or kept and the target nerve is repeatedly stimulated.

If in the third step 103, no activation of the target tissue is sensed, in a series of sub-steps the position of the electro-magnetic field and the field strength of the electro-magnetic field are automatically varied as follows: In a first sub-step 103$i$, the position of the coils is adjusted by tilting the coils to a predefined extent. Then, in a second sub-step 103$ii$, it is sensed again if the target tissue is activated. If this is the case, the fourth step 104 is performed as described above. If again no activation is sensed, the field strength of the electro-magnetic field is adjusted in a third sub-step 103$iii$. After that, in a fourth sub-step 103$iv$, it is again sensed if the target tissue is activated. If this is the case, the method is proceeded with the fourth step 104 as described above. If again no activation is sensed, the sequence of sub-steps is repeated.

In FIG. 11 a second embodiment of a method of activating a target tissue in a human or animal body via its muscular or neural system according to the invention is shown. The second method is similar to the first method described above wherein a tracking of movements of involved components and particularly of the body is included.

In particular, in a first step 201, coils are positioned at the human or animal body close to a target nerve. In a second step 202, a tracker is positioned close to the target tissue such that the target tissue is in a monitoring area of the tracker. In a third step 203, a spatial electro-magnetic field having a targeted shape is generated by means of the coils. In a fourth step 204, it is sensed if the target tissue associated to the target nerve is activated. If this is the case, in a fifth step 205, the position of the coils and the intensity of the electro-magnetic field are frozen or kept and the target nerve is repeatedly stimulated.

If in the fourth step 204 no activation of the target tissue is sensed, in a series of sub-steps, the position of the electro-magnetic field and the field strength of the electro-magnetic field are automatically varied as follows: In a first sub-step 204$i$, the position of the coils is adjusted by tilting the coils to a predefined extent. Then, in a second sub-step 204$ii$, it is sensed again if the target tissue is activated. If this is the case, the fifth step 205 is performed as described above. If again no activation is sensed, the field strength of the electro-magnetic field is adjusted in a third sub-step 204$iii$. After that, in a fourth sub-step 204$iv$, it is again sensed if the target tissue is activated. If this is the case, the method is proceeded with the fifth step 205 as described above. If again no activation is sensed, the sequence of sub-steps is repeated.

After stopping automatic variation of the coils and freezing the electro-magnetic field in step 205, relocation of the tracker indicating a movement of the body is monitored in a sixth step 206. If no relocation is detected, the method is continued at step 205. If however a relocation is detected, in an eighth step 208 an alarm is provided.

FIG. 12 shows a third embodiment of a method of activating a target tissue in a human or animal body via its muscular or neural system according to the invention. The third method is similar to the second method described above wherein automatic re-setup of the electro-magnetic field is involved when a relocation of the body relative to the coils is detected.

In particular, in a first step 301, coils are initially positioned at the human or animal body close to a target nerve. In a second step 302, a tracker is positioned close to the target tissue such that the target tissue is in a monitoring area of the tracker. In a third step 303, an initial electro-magnetic field having a targeted shape is generated by means of the coils. In a fourth step 304, it is sensed if the target tissue associated to the target nerve is activated. If this is the case, in a fifth step 305, the position of the coils and the intensity of the electro-magnetic field are frozen or kept and the target nerve is repeatedly stimulated.

If in the fourth step 304 no activation of the target tissue is sensed, in a series of sub-steps the position of the electro-magnetic field and the field strength of the electro-magnetic field are automatically varied as follows: In a first sub-step 304$i$, the position of the coils is adjusted by tilting the coils to a predefined extent. Then, in a second sub-step 304$ii$, it is sensed again if the target tissue is activated. If this is the case, the fifth step 305 is performed as described above. If again no activation is sensed, the field strength of the electro-magnetic field is adjusted in a third sub-step 304$iii$. After that, in a fourth sub-step 304$iv$, it is again sensed if the target tissue is activated. If this is the case, the method is proceeded with the fifth step 305 as described above. If again no activation is sensed, the sequence of sub-steps is repeated.

After stopping automatic variation of the coils and freezing the electro-magnetic field in step 305, relocation of the tracker indicating a movement of the body is monitored in a sixth step 306. If no relocation is detected, the method is continued at step 305. If however a relocation is detected, in an eighth step 308 the position of the coils and the field strength of the electro-magnetic field are reset to the same initial position and field strength as in steps 301 and 303. Then, in a ninth step 309, the coils are re-tilted and the electro-magnetic field readjusted into an expected position and field strength in accordance with the detected relocation. Thereby, the amount and direction of relocation are considered. After that, the method is continued at sub-step 304ii of the sequence of sub-steps.

This description and the accompanying drawings that illustrate aspects and embodiments of the present invention should not be taken as limiting—the claims defining the protected invention. In other words, while the invention has been illustrated and described in detail in the drawings and foregoing description, such illustration and description are to be considered illustrative or exemplary and not restrictive. Various mechanical, compositional, structural, electrical, and operational changes may be made without departing from the spirit and scope of this description and the claims. In some instances, well-known circuits, structures and techniques have not been shown in detail in order not to obscure the invention. Thus, it will be understood that changes and modifications may be made by those of ordinary skill within the scope and spirit of the following claims. In particular, the present invention covers further embodiments with any combination of features from different embodiments described above and below.

The disclosure also covers all further features shown in the Figs. individually although they may not have been described in the afore or following description. Also, single alternatives of the embodiments described in the figures and the description and single alternatives of features thereof can be disclaimed from the subject matter of the invention or from disclosed subject matter. The disclosure comprises subject matter consisting of the features defined in the claims or the exemplary embodiments as well as subject matter comprising said features.

Furthermore, in the claims the word "comprising" does not exclude other elements or steps, and the indefinite article "a" or "an" does not exclude a plurality. A single unit or step may fulfil the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Components described as coupled or connected may be electrically or mechanically directly coupled, or they may be indirectly coupled via one or more intermediate components. Any reference signs in the claims should not be construed as limiting the scope.

The invention claimed is:

1. An electro-magnetic induction device for activating a diaphragm of a human or animal body when being ventilated by a ventilation machine, the electro-magnetic induction device comprising:
    an electro-magnetic field generator with a coil design configured to generate a spatial electro-magnetic field having a targeted shape allowing for specifically stimulating one or both Phrenic nerves of a neural system of the human or animal body while lowering or preventing stimulation of other nerves or tissue neighboring, surrounding, or overlapping a Phrenic nerve of the one or both Phrenic nerves;
    a mounting arrangement configured to hold the coil design at a neck of the human or animal body such that one or both Phrenic nerves of the neural system of the human or animal body can be reached by the targeted shape of the electro-magnetic field generated by the coil design of the electro-magnetic field generator;
    a sensor member configured to detect an activation of the diaphragm of the human or animal body, wherein the sensor member comprises a flow sensor having an adaptor connectable to a respiratory system of the human or animal body;
    an electro-magnetic field adjustment mechanism configured to adjust a position of the electro-magnetic field generated by the coil design;
    a calibration unit in communication with the sensor member and with the electro-magnetic field adjustment mechanism, wherein the calibration unit is configured
        to control the electro-magnetic field adjustment mechanism to vary the position of the electro-magnetic field generated by the coil design,
        to receive an activation feedback signal from the sensor member upon detection of the activation of the diaphragm of the human or animal body, and
        to control the electro-magnetic field adjustment mechanism to stop variation of the position of the electro-magnetic field generated by the coil design when the activation feedback signal is received; and
    a controller in communication with the flow sensor and configured to regulate the activation of the diaphragm in coordination with a breathing scheme such that activation of the diaphragm via the one or both Phrenic nerves is coordinated with the ventilation of the human or animal body.

2. The electro-magnetic induction device of claim 1, wherein the mounting arrangement comprises a repositioning structure configured to automatically change a position of the coil design of the electro-magnetic field generator relative to the human or animal body when being held at the human or animal body.

3. The electro-magnetic induction device of claim 2, wherein
    the electro-magnetic field adjustment mechanism comprises the repositioning structure of the mounting arrangement and the calibration unit is configured to automatically vary the position of the electro-magnetic field by inducing the repositioning structure to automatically change the position of the coil design relative to the human or animal body, and/or
    the repositioning structure of the mounting arrangement comprises a tilting mechanism configured to tilt the coil design of the electro-magnetic field generator relative to the human or animal body when being held at the human or animal body.

4. The electro-magnetic induction device of claim 3, wherein the tilting mechanism is a joint.

5. The electro-magnetic induction device of claim 1, wherein the electro-magnetic field generator comprises an array of coils including the coil design, wherein
    the electro-magnetic field adjustment mechanism comprises the array of coils of the electro-magnetic field generator and the calibration unit is configured to automatically vary the position of the electro-magnetic field by inducing the electro-magnetic field adjustment mechanism to automatically empower different coil combinations of the array of coils, and/or coils of the array of coils preferably overlap, and/or the array of coils of the electro-magnetic field generator preferably are arranged to generate a plurality of electro-magnetic fields each having a targeted shape, the array of coils being arranged such that the plurality of electro-magnetic fields overlap and generate an accumulated intensity.

6. The electro-magnetic induction device of claim 1, wherein the sensor member comprises at least one electrode configured to be attached to the human or animal body such that it senses an activity of the diaphragm of the human or animal body, and/or a pressure sensor having an adaptor connectable to a respiratory system of the human or animal body, the pressure sensor being configured to detect a pressure change induced by an activity of the diaphragm of the human or animal body.

7. The electro-magnetic induction device of claim 1, wherein the mounting arrangement comprises an arc member arrangeable in distance around the neck of the human or animal body, the coil design of the electro-magnetic field generator being held at the arc member of the mounting arrangement, and wherein the arc member is equipped with an access passage.

8. The electro-magnetic induction device of claim 1, wherein the electro-magnetic field adjustment mechanism is configured to automatically adjust a field strength of the electro-magnetic field generated by the coil design and the calibration unit is configured to control the electro-magnetic field adjustment mechanism to automatically vary the field strength of the electro-magnetic field generated by the coil design and, optionally, to control the electro-magnetic field adjustment mechanism to automatically stop variation of the field strength of the electro-magnetic field generated by the coil design when the activation feedback is received, and/or to automatically adjust temporal characteristics of the electro-magnetic field and the calibration unit is configured to control the electro-magnetic field adjustment mechanism to automatically vary the temporal characteristics of the electro-magnetic field and, optionally, to control the electro-magnetic field adjustment mechanism to automatically stop variation of the temporal characteristics of the electro-magnetic field generated by the coil design when the activation feedback is received.

9. The electro-magnetic induction device of claim 1, comprising a tracker configured to detect a movement of the human or animal body relative to the coil design of the electro-magnetic field generator and to automatically change the position of the electro-magnetic field to compensate the detected movement of the human or animal body relative to the coil design of the electro-magnetic field generator.

10. The electro-magnetic induction device of claim 9, comprising an alarm unit, wherein the tracker is connected to the alarm unit and configured to activate the alarm unit when the detected movement exceeds a range of compensation achievable by changing the position of the electro-magnetic field generated by the coil design via the electro-magnetic field adjustment mechanism.

11. The electro-magnetic induction device of claim 1, wherein the calibration unit is configured to control the electro-magnetic field generator to generate the electro-magnetic field in pulses while the position of the electro-magnetic field generated by the coil design is varied, and to control the electro-magnetic field generator to generate the electro-magnetic field as a train of electro-magnetic field pulses when variation of the position of the electro-magnetic field generated by the coil design is stopped, wherein the calibration unit preferably is configured to control the electro-magnetic field generator to generate the electro-magnetic field as the train of electro-magnetic field pulses with an initially lower field strength and then increasing field strength than the electro-magnetic field in pulses.

12. The electro-magnetic induction device of claim 1, wherein the activation feedback signal comprises plural responses of activation of the diaphragm of the human or animal body each associated to one specific position of a target area of the electro-magnetic field generated by the coil design, and the calibration unit is configured to control the electro-magnetic field adjustment mechanism to adjust the position of the target area of the electro-magnetic field to the specific position associated to a strongest or most appropriate of the plural responses of the activation feedback signal, when the activation feedback signal is received.

13. The electro-magnetic induction device of claim 1, wherein the activation feedback signal comprises plural responses of activation of the diaphragm of the human or animal body each associated to one specific position of the electro-magnetic field generated by the coil design, and the calibration unit is configured to control the electro-magnetic field adjustment mechanism to adjust the position of the electro-magnetic field to the specific position associated to a most appropriate response characteristic of the plural responses of the activation feedback signal, when the activation feedback signal is received, and/or to adjust temporal field characteristics to the specific position and temporal settings associated to the most appropriate of the plural responses of the activation feedback signal, when the activation feedback signal is received, and/or to adjust temporal field characteristics to the specific position and temporal settings associated to the most appropriate response characteristic of the plural responses of the activation feedback signal, when the activation feedback signal is received.

14. A method of transcutaneous electro-magnetic induction of one or more Phrenic nerves for a diagnostic purpose to assess diaphragm function, or of repetitive regular transcutaneous electro-magnetic induction of one or more Phrenic nerves for therapeutic use in patients with no spontaneous breath, or of repeated transcutaneous electro-magnetic induction of one or more Phrenic nerves for therapeutic use in patients with no or insufficient spontaneous diaphragm contractions who have at least a partly intact Phrenic nerve, by means of an electro-magnetic induction device according to claim 1.

15. The method of claim 14, wherein the therapeutic use in patients with no spontaneous breath is reanimation and keeping alive patients who have no function of a respiratory center.

16. The electro-magnetic induction device of claim 1, wherein the flow sensor is configured to detect an air flow change induced by an activity of the diaphragm of the human or animal body.

17. The electro-magnetic induction device of claim 16, wherein the adaptor of the flow sensor of the sensor member is configured to be connected to a mouth and/or a nose of the human or animal body.

18. A process of manufacturing an electro-magnetic induction device for activating a diaphragm in a human or animal body via its muscular or neural system when being ventilated by a ventilation machine, comprising:

assembling to the electro-magnetic induction device an electro-magnetic field generator with coil design configured to generate a spatial electro-magnetic field having a targeted shape allowing for specifically stimulating one or both Phrenic nerves of the neural system of the human or animal body while lowering or preventing stimulation of other nerves or tissue neighboring, surrounding or overlapping a Phrenic nerve of the one or both Phrenic nerves, a mounting arrangement configured to hold the coil design at a neck of the human or animal body such that one or both Phrenic nerves of the neural system of the human or animal body can be reached by the electro-magnetic field generated by the coil design of the electro-magnetic field generator, a sensor member configured to detect an activation of the diaphragm of the human or animal body, wherein the sensor member comprises a flow sensor having an adaptor connectable to a respiratory system of the human or animal body, a controller in communication with the flow sensor, an electro-magnetic field adjustment mechanism configured to adjust a position of the electro-magnetic field generated by the coil design, and a calibration unit in communication with the sensor member and with the electro-magnetic field adjustment mechanism; and configuring the calibration unit, to control the electro-magnetic field adjustment mechanism to vary the position of the electro-magnetic field generated by the coil design, to receive an activation feedback signal from the sensor member upon detection of the activation of the diaphragm of the human or animal body, and to control the electro-magnetic field adjustment mechanism to stop variation of the position of the electro-magnetic field generated by the coil design when the activation feedback is received; and configuring the controller to regulate the activation of the diaphragm in coordination with a breathing scheme such that activation of the diaphragm via the one or both Phrenic nerves is coordinated with the ventilation of the human or animal body.

19. The process of claim 18, comprising providing the mounting arrangement with a repositioning structure configured to automatically change a position of the coil design of the electro-magnetic field generator relative to the human or animal body when being held at the human or animal body, comprising providing the electro-magnetic field adjustment mechanism with the repositioning structure of the mounting arrangement and configuring the calibration unit to automatically vary the position of the electro-magnetic field by inducing the repositioning structure to automatically change the position of the coil design relative to the human or animal body, and/or, providing the repositioning structure of the mounting arrangement with a tilting mechanism configured to tilt the coil design of the electro-magnetic field generator relative to the human or animal body when being held at the human or animal body.

20. The process of claim 19, wherein the tilting mechanism is a joint.

21. The process of claim 18, comprising providing the electro-magnetic field generator with an array of coils including the coil design, wherein coils of the array of coils preferably overlap, comprising providing the electro-magnetic field adjustment mechanism with the array of coils of the electro-magnetic field generator and configuring the calibration unit to automatically vary the electro-magnetic field by inducing the electro-magnetic field adjustment mechanism to automatically empower different coil combinations of the array of coils, and/or arranging the array of coils of the electro-magnetic field generator to generate a plurality of electro-magnetic fields each having a targeted shape, the array of coils being arranged such that the plurality of electro-magnetic fields overlap and generate an accumulated intensity.

22. The process of claim 18, comprising providing the sensor member with at least one electrode configured to be attached to the human or animal body such that it senses an activity of the diaphragm of the human or animal body, and/or configuring the adaptor of the flow sensor of the sensor member to be connected to a mouth and/or a nose of the human or animal body, and/or comprising providing the mounting arrangement with an arc member arrangeable in distance around the neck of the human or animal body, the coil design of the electro-magnetic field generator being held at the arc member of the mounting arrangement, wherein the arc member preferably is equipped with an access passage, and/or assembling a tracker into the electro-magnetic induction device, wherein the tracker is configured to detect a movement of the human or animal body relative to the coil design of the electro-magnetic field generator and to automatically change the position of the electro-magnetic field to compensate the detected movement of the human or animal body relative to the coil design of the electro-magnetic field generator, and/or configuring the electro-magnetic field adjustment mechanism to automatically adjust a field strength of the electro-magnetic field generated by the coil design and configuring the calibration unit to control the electro-magnetic field adjustment mechanism to automatically vary the field strength of the electro-magnetic field generated by the coil design and to control the electro-magnetic field adjustment mechanism to automatically stop variation of the field strength of the electro-magnetic field generated by the coil design when the activation feedback is received, and/or assembling an alarm unit into the electro-magnetic induction device, wherein the tracker is connected to the alarm unit and configured to activate the alarm unit when the detected movement exceeds a range of compensation achievable by changing the position of the electro-magnetic field generated by the coil design via the electro-magnetic field adjustment mechanism, and/or configuring the electro-magnetic field adjustment mechanism to automatically adjust temporal characteristics of the electro-magnetic field and configuring the calibration unit to control the electro-magnetic field adjustment mechanism to automatically vary the temporal characteristics of the electro-magnetic field and, optionally, to control the electro-magnetic field adjustment mechanism to automatically stop variation of the temporal characteristics of the electro-magnetic field generated by the coil design when the activation feedback is received.

23. The process of claim 18, comprising configuring the calibration unit
- to control the electro-magnetic field generator to generate the electro-magnetic field in pulses while the position of the electro-magnetic field generated by the coil design is varied, and/or
- to control the electro-magnetic field generator to generate the electro-magnetic field as a train when variation of the position of the electro-magnetic field generated by the coil design is stopped, and/or
- to control the electro-magnetic field generator to generate the electro-magnetic field as a train with an initially lower and then increasing field strength than the electro-magnetic field in pulses.

24. The process of claim 18, wherein the activation feedback signal comprises plural responses of activation of the diaphragm of the human or animal body each associated to one specific position of the electro-magnetic field generated by the coil design, comprising configuring the calibration unit to control the electro-magnetic field adjustment mechanism to adjust the position of the electro-magnetic field to the specific position associated to a most appropriate response characteristic of the plural responses of the activation feedback signal, when the activation feedback signal is received, and/or to adjust temporal field characteristics to the specific position and temporal settings associated to a most appropriate of the plural responses of the activation feedback signal, when the activation feedback signal is received, and/or to adjust temporal field characteristics to the specific position and temporal settings associated to the most appropriate response characteristic of the plural responses of the activation feedback signal, when the activation feedback signal is received.

25. The process of claim 18, wherein the flow sensor is configured to detect an air flow change induced by an activity of the diaphragm of the human or animal body.

* * * * *